United States Patent

Hirano et al.

[11] Patent Number: 5,939,509
[45] Date of Patent: Aug. 17, 1999

[54] EPOXY RESIN, RESIN COMPOSITION, AND RESIN-ENCAPSULATED SEMICONDUCTOR DEVICE

[75] Inventors: Yasuhiro Hirano; Masatsugu Akiba; Akira Yokota; Hiroshi Nakamura; Shigeki Naitoh, all of Ibaraki, Japan

[73] Assignee: Sumitomo Chemical Company, Ltd., Osaka, Japan

[21] Appl. No.: 08/879,600

[22] Filed: Jun. 20, 1997

Related U.S. Application Data

[62] Division of application No. 08/639,506, Apr. 29, 1996.

[30] Foreign Application Priority Data

| Apr. 27, 1995 | [JP] | Japan | 7-104464 |
| Apr. 28, 1995 | [JP] | Japan | 7-106768 |
| Apr. 28, 1995 | [JP] | Japan | 7-106769 |
| May 2, 1995 | [JP] | Japan | 7-108418 |

[51] Int. Cl.$^6$ .................. C08G 59/16
[52] U.S. Cl. ............... 528/101; 568/729
[58] Field of Search ............ 568/729; 528/101

[56] References Cited

U.S. PATENT DOCUMENTS

| 3,624,162 | 11/1971 | Sieber .................. 568/729 |
| 4,156,787 | 5/1979 | Coleman ................ 568/729 |
| 4,189,610 | 2/1980 | Coleman ................ 568/646 |
| 4,762,901 | 8/1988 | Dhein et al. . |
| 5,262,509 | 11/1993 | Hefner, Jr. et al. . |
| 5,264,502 | 11/1993 | Hefner, Jr. et al. . |
| 5,266,405 | 11/1993 | Kirchmeyer et al. ........ 428/413 |
| 5,266,660 | 11/1993 | Hefner, Jr. et al. . |
| 5,268,434 | 12/1993 | Hefner, Jr. et al. . |
| 5,270,404 | 12/1993 | Earls et al. . |
| 5,270,405 | 12/1993 | Earls et al. . |
| 5,276,184 | 1/1994 | Hefner, Jr. et al. . |
| 5,292,831 | 3/1994 | Earls et al. . |
| 5,314,693 | 5/1994 | Suga . |
| 5,360,884 | 11/1994 | Hefner, Jr. et al. . |
| 5,414,150 | 5/1995 | Hefner, Jr. et al. ......... 568/729 |
| 5,415,125 | 5/1995 | Fujita et al. . |
| 5,463,091 | 10/1995 | Earls et al. . |

FOREIGN PATENT DOCUMENTS

| 0 379 057 a2 | 7/1990 | European Pat. Off. . |
| 0 478 918 A2 | 4/1992 | European Pat. Off. . |
| 36 22613 A1 | 1/1988 | Germany . |
| 63-23931 | 2/1988 | Japan . |
| 64-56721 | 3/1989 | Japan . |
| 64-85215 | 3/1989 | Japan . |
| 2-275872 | 11/1990 | Japan . |
| 4-233933 | 8/1992 | Japan . |

OTHER PUBLICATIONS

Patent Abstracts of Japan, vol. 016, No. 358 (C–0970), Aug. 4, 1992.
Patent Abstracts of Japan, vol. 016, No. 537 (C–1003), Nov. 6, 1992.
Proceed. 3rd Next–generation Industrial Infrastructure Technology Symposium (1985).
Sieber, von Rolf, 'Reaktionen von Chloracetaldehyd mit aromatischen Kohlenwasserstoffen, Phenolen und Phenolathern', Liebiggs Ann. Chem. 730, pp. 31–46 (1969).
Methoden Der Organischen Chemie, (Houben–Weyl) Band IV/1c, Phenole, Teil 2, pp. 1034–1035 (1976).

*Primary Examiner*—Melvyn Marquis
*Assistant Examiner*—D. Aylward
*Attorney, Agent, or Firm*—Pillsbury Madison & Sutro LLP

[57] ABSTRACT

The stilbene epoxy resin having two different aryl groups and an epoxy resin mixture including this stilbene epoxy resin have lower melting points than those of the stilbene epoxy resin having two identical aryl groups and the epoxy resin mixture of the latter stilbene epoxy resin. Compared with the conventional resins, the present resin or resin mixture has improved working and molding properties, which shortens the time required for the molding and working process, resulting in economic advantages and a preferred affect on productivity. The present epoxy resin or resin mixture is preferably used as an adhesive, a coating, an insulating material, an electrical or electronic material for laminated sheets or the like. It is especially suited for use as material for encapsulating electronic parts.

8 Claims, No Drawings

EPOXY RESIN, RESIN COMPOSITION, AND RESIN-ENCAPSULATED SEMICONDUCTOR DEVICE

This is a division of application Ser. No. 08/639,506, filed Apr. 29, 1996.

FIELD OF THE INVENTION

The present invention relates to a bisphenol preferably used as adhesive, coating, and electrical or electronic materials such as insulating materials or laminated sheets or the like, and especially as raw materials or intermediates of electronic parts, as well as to a method of manufacturing the same.

The present invention also relates to an epoxy resin composition for encapsulating electronic parts and resin-encapsulated semiconductor device using the same.

BACKGROUND OF THE INVENTION

Transfer molding using an epoxy resin composition is typically adopted as an economically advantageous means for encapsulating semiconductor devices, such as LSIs, ICs, and transistors.

Recently, resin-encapsulated LSIs are directly soaked in a solder bath for surface mounting. In the surface mounting process, the encapsulating material is exposed to a temperature of 200° C. or even higher. The water absorbed in the encapsulating material is accordingly expanded and causes cracks in the encapsulating package of the semiconductor devices.

The epoxy resin encapsulating material is accordingly required to have low moisture absorption characteristics and improved cracking resistance. A widely used encapsulating material includes glycidyl ether of o-cresol novolak as an epoxy resin and phenol novolak as a curing agent. This widely used encapsulating material must be stored in moisture-resistant packaging to avoid the above problems. To solve the above mentioned problems, especially to obtain low moisture absorption characteristics, low viscosity epoxy resins which can contain large amount of fillers have been developed and used for practical applications; for example, a glycidyl ether epoxy resin having a tetramethylbiphenyl skeleton.

To improve the physical properties of the encapsulating material, the technique of improving the mechanical properties of cured resin is effective. A known method of improving the mechanical properties of cured objects of thermosetting resin controls the molecular orientation in the cured objects. There is a prior art document which is related to a stilbene skeleton-containing epoxy resin. It has been reported that polymerization of a liquid crystal properties-possessing epoxy compound in the liquid crystal state in the presence of a small quantity of catalyst yields a crosslinked body which retains the liquid crystal structure and that polymerization in an electric field of specific conditions serves to orientate the liquid crystal domain as seen from page 182 in the Proceedings of the 3rd Next-generation Industrial Infrastructure Technology Symposium (1985). In this report, epoxidized 4,4'-dihydroxy-&A-cyanostilbene is shown as an example of the compound having liquid crystal properties.

Some epoxy compounds including the rod-like structure of carbon—carbon double bond, carbon-nitrogen double bond, nitrogen—nitrogen double bond, or the like, which is different from the structure of the present invention, have been proposed as compounds possessing excellent physical properties in Japanese Patent Laid-open No. S-64-56721 and Japanese Patent Laid-open No. H-1-85215.

A method for manufacturing structural members has been proposed, in which the structural members were cured with using a compound having a liquid crystal properties-donating component in the molecular structure thereof, while maintaining the liquid crystal structure, thereby improving the mechanical properties as seen from U.S. Pat. No. 4,762,901, German Patent No. 3,622,613, and Japanese Patent Laid-open No. S-63-23931. A glycidyl ether of bisphenol compound having a non-substituted or alkyl group-substituted stilbene skeleton, or preferably having a stilbene skeleton with symmetrically substituted methyl groups, is given just as an example of such liquid crystal properties-containing compounds with other known compounds. Some stilbene bisphenol compounds having identical aryl substituents bound to the carbon-carbon double bond have also been reported previously. Preparation and physical properties of the compounds, such as 4,4'-dihydroxystilbene, 4,4'-dihydroxy-3,3'-dimethylstilbene, 4,4'-dihydroxy-3,3',5,5'-tetramethylstilbene, have been disclosed (von Rolf H. Sieber, Liebigs Ann. Chem. 730, 31–46 (1969)). A method of preparing 4,4'-dihydroxy-&A-methylstilbene has been described in METHODEN DER ORGANISCHEN CHEMIE (HOUBEN-WEYL) BAND IV/1c Phenol Teil 2 P1034.

Epoxy resins having liquid crystal properties or the rod-like structure for the improved mechanical properties have also been proposed as seen from Japanese Patent Laid-open No. H-2-275872. Examples of hydroxyl group-containing compounds for epoxidation are 4,4'-dihydroxy-&A-methylstilbene, 4,4'-dihydroxystilbene, 4,4'-dihydroxy-3,3', 5,5'-tetrabromostilbene, and 4,4'-dihydroxy-3,3',5,5'-tetramethylstilbene. Resin compositions of the epoxy resin having the liquid crystal properties-developing functional group or the rod-like structure and the compound having active hydrogen have also been proposed for improving the physical properties as seen from Japanese Patent Laid-open No. H4-233933, U.S. Pat. No. 5,292,831, U.S. Pat. No. 5,270,405, U.S. Pat. No. 5,270,404, and U.S. Pat. No. 5,266,660. In the specifications of these patents or patent application, orientation of molecules in a cured object with the given epoxy compound has been proposed in order to improve the physical properties of the cured object.

Conventional resins for encapsulant, such as, for example, encapsulating materials comprising a glycidyl ether of o-cresol novolak, have substantially-balanced heat resistance and molding properties, but possess poorer physical properties as encapsulants than those of biphenyl epoxy resins. The biphenyl epoxy resins have low moisture absorption characteristics and excellent physical properties as the encapsulating material for surface mounting, but have undesirably low heat resistance and which results in package cracks under high humidity condition.

The conventional stilbene epoxy resins show excellent curing properties but have high melting points and poorer working properties in the process of mixing the epoxy resin component with inorganic fillers or in the molding process. For example, glycidyl ethers of 4,4'-dihydroxystilbene, 4,4'-dihydroxy-3,3'-dimethylstilbene, and 4,4'-dihydroxy-3,3',5, 5'-tetramethylstilbene have high melting points of 208 to 215° C., 150° C., and 151° C., respectively, and suffer from rather bad working properties. In fact, the epoxy resin of 4,4'-dihydroxystilbene can not be used for encapsulating semiconductors under the conditions practiced with the current production equipment.

Semiconductor-encapsulating materials including thermosetting resins are formed to packages within a time period of 60 through 90 seconds. The cured objects of such material have a three-dimensional crosslinked structure without any specific molecular orientation as disclosed in the prior art described above. The prior arts above have been proposed to further improve the physical properties of cured objects by introducing a specific orientation to the cured structure. To introduce the liquid crystal state or the specific molecular orientation to cured objects, molding under the specified temperature conditions or external control of the molding conditions by means of an electric field or magnetic field is required. The cured objects having the specific molecular orientation have different strengths and thermal expansion coefficients according to the direction of molding. When stress is applied in the form of tests, such as the solder heat resistance test after water absorption, it is concentrated on specific portions of a package having low strength and eventually causes cracks in the package.

The cured object prepared from the resin composition according to the present invention is only required to have a cured structure of substantially equivalent to that of the conventional thermosetting epoxy resin composition, and is not a cured object including a specific molecular orientation and having the deteriorating physical properties according to the direction.

Another technique to further accelerate the orientation of molecules are proposed in which the epoxy compound having a liquid crystal properties-developing group is previously reacted with the compound having active hydrogen. This technique heightens the degree of polymerization of the resin composition, and accordingly increases the melt viscosity of the resin composition including inorganic fillers, which causes difficulties in the molding process. The present invention does not require any specific pre-reaction of the epoxy component with the epoxy curing component, and accordingly has no specific cured structure observed as a result of such pre-reaction.

The conventional stilbene epoxy resin, having a high melting point and low solubility in an organic solvent, is hardly applied to laminated sheets, composite material, or coating material.

SUMMARY OF THE INVENTION

An object of the present invention is to provide a stilbene bisphenol as an intermediate of a stilbene epoxy resin having a relatively low melting point and favorable solubility in a solvent, as well as a method of manufacturing such a stilbene bisphenol.

Another object of the present invention is to provide a stilbene epoxy resin having a low melting point and favorable solubility in a solvent as well as a method of manufacturing such a stilbene epoxy resin.

Still another object of the present invention is to provide an epoxy resin composition, which is preferably used as a high performance encapsulating material with high reliability and is easily applicable to the conventional semiconductor encapsulating equipment and process without changing the molding conditions and time and the working properties of the conventional epoxy resin.

A still further object is to provide an epoxy resin composition having excellent working properties, low moisture absorption characteristics, and favorable heat resistance, and especially possesses high resistance against package cracks without any specific pre-reactions or curing conditions.

The present invention includes a number of embodiments, one which is directed to a stilbene bisphenol represented by the general formula (1), in which two different aryl groups are bound to a carbon—carbon double bond,

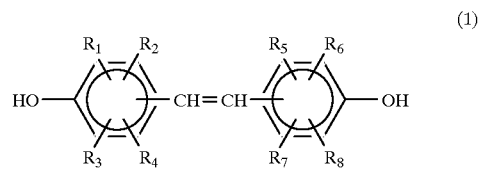

wherein $R_1$ through $R_8$ independently represent acyclic or cyclic alkyl groups having 1 through 6 carbon atoms, hydrogen atom or halogen atoms.

The invention also includes a stilbene epoxy resin represented by the general formula (2), in which two different aryl groups are bound to a carbon—carbon double bond,

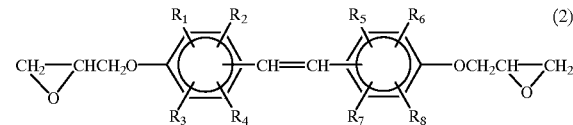

wherein $R_1$ through $R_8$ independently represent acyclic or cyclic alkyl groups having 1 through 6 carbon atoms, hydrogen atom or halogen atoms.

Another embodiment concerns a bisphenol mixture which comprises, for instance, a stilbene bisphenol represented by the general formula (1), and a stilbene bisphenol represented by the general formula (3) given below in which two identical aryl groups are bound to a carbon—carbon double bond,

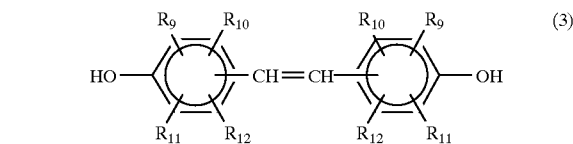

wherein $R_9$ through $R_{12}$ independently represent acyclic or cyclic alkyl groups having 1 through 6 carbon atoms, hydrogen atom or halogen atoms. The bisphenol mixture can be prepared, for instance, by the combination of steps comprising conducting a dehydrochlorination reaction of a 1,1-bis(hydroxyphenyl)-2-chloroethane derivative, wherein the derivative is obtained by a reaction of two or more phenols with chloroacetaldehyde in the presence of an acid substance, and subjecting the reaction product to a rearrangement reaction in the presence of a basic substance.

A further embodiment is an epoxy resin mixture having a melting point of not higher than 150° C. which comprises a stilbene epoxy resin represented by formula (2), and a stilbene epoxy resin represented by the general formula (4) given below in which two identical aryl groups are bound to a carbon—carbon double bond,

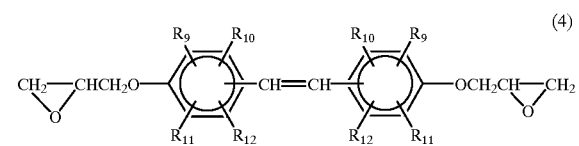

wherein $R_9$ through $R_{12}$ independently represent acyclic or cyclic alkyl groups having 1 through 6 carbon atoms, hydrogen atom or halogen atoms. The melt viscosity of this epoxy resin mixture is generally not greater than 1 poise at 150° C.

Related method embodiments include preparing this epoxy resin mixture by the combination of steps comprising conducting a dehydrochlorination reaction of 1,1-bis (hydroxyphenyl-2-chloroethane derivative, which is obtained by a reaction of two or more phenols with chloroacetaldehyde in the presence of an acid substance, in the presence of a basic substance to yield a dihydroxystilbene derivative; and reacting the dihydroxystilbene derivative with an epihalohydrin in the presence of a basic substance. Another method embodiment involves preparing the epoxy resin mixture by the combination of steps of preparing a 1,1-bis(hydroxyphenyl) -2-chloroethane derivative, which is obtained by a reaction of two or more phenols with chloroacetaldehyde in the presence of an acid substance, and allowing it to react with an epihalohydrin in the presence of a basic substance. In these methods for preparing an epoxy resin mixture, the phenols can comprise two or more phenols selected among the group consisting of 2,6-xylenol, 2,4-xylenol, 3-methyl-6-t-butylphenol, and 2-methyl-6-t-butylphenol. More particularly, the phenols comprise a mixture of 2,6-xylenol and 3-methyl-6-t-butylphenol.

Still further, a curable epoxy resin composition embodiment according to the present invention comprises the combination of (A) a stilbene epoxy resin in accordance represented by formula (2) or an epoxy resin mixture which comprises a mixture of resins represented by general formulas (2) and (4); (B) a phenolic epoxy curing agent; and, optionally, (C) an inorganic filler. The stilbene epoxy resin or epoxy resin mixture can have a melting point of not higher than 150° C. In a curable epoxy resin composition, which contains an epoxy component represented by formula (2), $R_1$ can represent a t-butyl group, and $R_5$ through $R_8$ can independently represent acyclic alkyl groups other than t-butyl group or cyclic alkyl groups having 1 through 6 carbon atoms, hydrogen atoms, or halogen atoms.

A more specific embodiment of the curable epoxy resin composition comprises an epoxy resin mixture of, for instance, a stilbene epoxy resin represented by the general formula (2) which comprises at least one resin selected from among glycidyl ether compounds of 3-t-butyl-2,4'-dihydroxy-3',5',6- trimethylstilbene and 3-t-butyl4,4'-dihydroxy-3',5',6-trimethyl-stilbene; and a stilbene epoxy resin represented by the general formula (4) which comprises at least one resin selected from among glycidyl ether compounds of 4,4'-dihydroxy-3,3',5,5'-tetramethylstilbene, 4,4'-dihydroxy-3,3'-di-t-butyl-6,6'-dimethylstilbene, 2,2'-dihydroxy-3,3'-di-t-butyl-6,6'-dimethylstilbene, and 2,4'-dihydroxy-3,3'-di-t-butyl-6,6'-dimethylstilbene.

A cured epoxy resin product is obtained by curing the curable epoxy resin composition.

A resin-encapsulated semiconductor device can be manufactured by encapsulating a semiconductor device (element) with an epoxy resin composition according to the present invention. The epoxy resin composition can include at least one inorganic filler.

DETAILED DESCRIPTION OF THE INVENTION

Suitable examples of the substituents $R_1$ through $R_{12}$ in the stilbene bisphenols represented by general formulas (1) and (3) and in the stilbene epoxy resins represented by general formulas (2) and (4) in the present invention include methyl group, ethyl group, propyl group, butyl group, amyl group, hexyl group, and cyclohexyl group (including the respective isomers) as well as chlorine atom and bromine atom. Methyl group, ethyl group, propyl group, and butyl group are particularly preferred because of the low melt viscosity of products and availability of material. By preference, in a stilbene bisphenol represented by formula (1), $R_1$ can represent t-butyl group, and $R_5$ through $R_8$ represent independently acyclic alkyl groups other than t-butyl group, cyclic alkyl groups, hydrogen atoms or halogen atoms. By preference, in a stilbene bisphenol represented by formula (2), $R_1$ can represent a t-butyl group, and $R_5$ through $R_8$ can represent acyclic alkyl groups other than t-butyl group, cyclic alkyl groups, hydrogen atoms or halogen atoms.

Suitable examples of the stilbene bisphenol of the present invention represented by general formula (1) given above and having two different aryl groups bound to a carbon—carbon double bond include 3-t-butyl-4,4'-dihydroxy-3'-methyl-stilbene, 3-t-butyl-4,4'-dihydroxy-5,3'-dimethyl-stilbene, 3-t-butyl-4,4'-dihydroxy-3',6-dimethylstilbene, 3-t-butyl-4,4'-dihydroxy-5-ethyl-3'-methylstilbene, 3-t-butyl-4, 4'-dihydroxy-3'-methyl-5-propylstilbene, 3-t-butyl-4,4'-dihydroxy-5-butyl-3'-methyl-stilbene, 3-t-butyl-4,4'-dihydroxy-5-amyl-3'-methyl-stilbene, 3-t-butyl-4,4'-dihydroxy-5-hexyl-3'-methylstilbene, 3-t-butyl-4,4'-dihydroxy-5-cyclohexyl-3'-methylstilbene, 3-t-butyl-4,4'-dihydroxy-3',5,5'-trimethyl-stilbene, 3-t-butyl-2,4'-dihydroxy-3',5',6-trimethylstilbene, 3-t-butyl-2,4'-dihydroxy-3',5',6-trimethylstilbene, 3-t-butyl-4,4'-dihydroxy-3',5-dimethyl-5'-propylstilbene, and 3-t-butyl-4, 4'-dihydroxy-3',6-dimethyl-5'-propylstilbene. Among these, 3-t-butyl-4,4'-dihydroxy-3',5,5'-trimethylstilbene, 3-t-butyl-2,4'-dihydroxy-3',5',6-trimethylstilbene, and 3-t-butyl-4,4'-dihydroxy-3',5',6-trimethylstilbene because of they are easily synthesized and, perform favorably, and are economical, i.e. a low material cost.

The stilbene epoxy resin of the present invention represented by general formula (2) and having two different aryl groups bound to a carbon—carbon double bond, include, for instance, glycidyl ether compounds of the above bisphenols.

Illustrative of the stilbene bisphenols of the present invention represented by general formula (3) and having two identical aryl groups bound to a carbon—carbon double bond are, among others, 4,4'-dihydroxy-3,3'-dimethylstilbene, 3,3'-diethyl-4,4'-dihydroxystilbene, 4,4'-dihydroxy-3,3'-dipropylstilbene, 3,3'-diamyl-4,4'-dihydroxystilbene, 3,3'-dihexyl-4,4'-dihydroxystilbene, 3,3'-dicyclohexyl-4,4'-dihydroxystilbene, 2,2'-dihydroxy-3,3',5, 5'-tetramethylstilbene, 4,4'-dihydroxy-3,3',5,5'-tetramethylstilbene, 4,4'-dihydroxy-3,3'-di-t-butylstilbene, 4,4'-dihydroxy-3,3'-di-t-butyl-5,5 '-dimethyl-stilbene, 4,4'-dihydroxy-3,3'-di-t-butyl-6,6'-dimethylstilbene, 2,2'-dihydroxy-3,3'-di-t-butyl-6,6'-dimethylstilbene, 2,4'-dihydroxy-3,3'-di-t-butyl-6,6'-dimethylstilbene, and 4,4'-dihydroxy-3,3',5,5'-tetra-t-butylstilbene. Among these, 2,2'-dihydroxy-3,3',5,5'-tetramethylstilbene, 4,4'-dihydroxy-3,3', 5,5'-tetramethylstilbene, 4,4'-dihydroxy-3,3'-di-t-butyl-5,5'-dimethylstilbene, 4,4'-dihydroxy-3,3'-di-t-butyl-6,6'-dimethyl-stilbene, 2,2'-dihydroxy-3,3'-di-t-butyl-6,6'-dimethylstilbene, and 2,4'-dihydroxy-3,3'-di-t-butyl-6,6'-dimethylstilbene are preferred because they are easily synthesized, perform favorably and are economical, i.e., a low material cost.

The stilbene epoxy resin of the present invention represented by general formula (4) given above and having two identical aryl groups bound to a carbon—carbon double bond, include glycidyl ether compounds of the above bisphenols.

The intermediate of the stilbene bisphenol of the present invention, that is, 1,1-bis(hydroxyphenyl)-2-chloroethane derivative, is obtained by the reaction of phenols with chloroacetaldehyde.

Various t-butyl group-containing phenols are available, include, among others, 3-methyl-6-t-butylphenol, 2-methyl-6-t-butylphenol, 2-t-butyl phenol, 2-ethyl-6-t-butyl phenol, 2-propyl-6-t-butyl phenol, 2,6-di-t-butylphenol, 2-isobutyl-6-t-butylphenol, 2-amyl-6-t-butylphenol, ((2-amyl-6-t-butyl-phenol)), 2-hexyl-6-t-butylphenol, and 2-cyclohexyl-6-t-butylphenol. Among these, 3-methyl-6-t-butylphenol and 2-methyl-6-t-butylphenol are preferred because of the favorable melting point of final products, availability of material, and lower material cost. The phenol need not contain a t-butyl group, and examples of these phenols include, for instance, cresol, xylenol, trimethylphenol, tetramethyl phenol, methylethylphenol, methyl propyl phenol, methyl isobutyl phenol, methyl hexylphenol, and methylcyclohexylphenol (and their isomers). Xylenol is preferred because of its favorable balance of performance and material cost.

Examples of the chloroacetaldehyde used in the present invention include chloroacetaldehyde, aqueous solutions of chloroacetaldehyde, acetals of chloroacetaldehyde, and trioxane-type trimers of chloroacetaldehyde. The amount of chloroacetaldehyde used is about 0.8 through about 1.4 moles, or preferably an equivalent mole, with respect to a total 1 mole of the phenols. An amount of chloroacetaldehyde less than this range causes the unreacted phenols to remain in the product, whereas the amount greater than this range often leads to polymerization of the product.

The reaction of phenols with chloroacetaldehyde is generally carried out in the presence of an acidic substance. Suitable examples of the acidic substance include, among others, inorganic acids, such as fuming sulfuric acid, concentrated sulfuric acid, aqueous sulfuric acid, concentrated hydrochloric acid, hydrogen chloride gas, aqueous hydrochloric acid, and trifluorosulfonic acid; organic acids, such as p-toluenesulfonic acid, chloroacetic acid, trichloroacetic acid, and trifluoroacetic acid; heteropolyacids; and acidic ion exchange resins. Concentrated sulfuric acid is particularly preferred, because it easily gives high-purity products. The amount of acidic substance used is about 0.1 through about 10 moles, and is preferably about 0.5 through about 2 moles, with respect to 1 mole of chloroacetaldehyde. The amount of acidic substance less than this range results in the slow reaction, whereas the amount greater than this range is of no additional effect.

The reaction can be conducted in the presence of a solvent. Suitable solvents for the reaction include, for instance, hydrocarbons like toluene and xylene, halogenated hydrocarbons like chlorobenzene, ethers like dioxane and tetrahydrofuran, alcohols like methanol and propanol, nonprotic polar solvents like dimethylsulfoxide, dimethylacetamide, and dimethylformamide, glycols like ethylene glycol and propylene glycol, and acidic solvents like acetic acid. Acetic acid is especially preferred. A single solvent or a mixture of suitable solvents can be used.

The amount of solvent used is 0.1 through 20 times, or preferably 0.5 through 10 times, the weight of phenols and chloroacetaldehyde. The amount of solvent less than this range makes precipitates deposited by the reaction interfere with smooth stirring, whereas the amount greater than this range lowers the yield and is economically disadvantageous.

The acidic substance may be added dropwise to the phenols and chloroacetaldehyde previously dissolved in the solvent, or alternatively, chloroacetaldehyde may be added dropwise to the phenols and acidic substance in a reaction vessel. The time required for the dropwise addition is generally about 0.5 hours through about 10 hours. The reaction continues for about 3 through about 24 hours after the dropwise addition. The reaction temperature is about −30 through about 60° C., and is preferably about −10 through about 40° C. The temperature lower than this range results in the slow reaction, whereas the temperature higher than this range significantly increases formation of impurities. After the reaction, the deposited precipitates are filtered off, washed with water, and dried under reduced pressure to yield 1,1-bis(hydroxyphenyl)-2-chloroethane derivative as an intermediate.

The intermediate is then subjected to a dehydrochlorination reaction and a rearrangement reaction. The 1,1-bis(hydroxyphenyl)-2-chloroethane derivative obtained is dissolved in a solvent and a basic substance, such as an aqueous solution of sodium hydroxide, is added dropwise to the solution to complete these reactions. Suitable solvents include hydrocarbons like toluene and xylene, halogenated hydrocarbons like chlorobenzene, ethers like dioxane and tetrahydrofuran, alcohols like methanol and propanol, nonprotic polar solvents like dimethylsulfoxide, dimethylacetamide, and dimethylformamide, glycols like ethylene glycol and propylene glycol, and acidic solvents like acetic acid. Alcohols, such as lower-alkyl alcohols like methanol and propanol, are especially preferred. A single solvent or a mixture of suitable solvents can be used.

The amount of solvent used is 0.1 through 20 times, or preferably 0.5 through 10 times, the weight of 1,1-bis(hydroxyphenyl)-2-chloroethane derivative. The amount of solvent less than this range makes salts deposited by the reaction interfere with smooth stirring, whereas the amount greater than this range lowers the yield and is economically disadvantageous.

The basic substance used for the reaction may be powder, pellets, or an aqueous solution of sodium hydroxide or potassium hydroxide, although an aqueous solution of sodium hydroxide is preferable because of its easy handling properties and low material cost. The amount of basic substance used is 1 through 5 moles, or preferably 1 through 2 moles, with respect to 1 mole of the 1,1-bis(hydroxyphenyl)-2-chloroethane derivative. The amount of basic substance less than this range causes unreacted material to remain in the product, whereas the amount greater than this range is of no additional effect.

The basic substance may be added dropwise to the 1,1-bis(hydroxyphenyl)-2-chloroethane derivative previously dissolved in the solvent, or alternatively, powder, solution or slurry of the 1,1-bis(hydroxyphenyl)-2-chloroethane derivative may be added dropwise to the basic substance ((phenols and acidic acid)) in a reaction vessel. The time required for the dropwise addition is generally about 0.5 hours through about 10 hours. The reaction continues for about 3 through about 24 hours after the dropwise addition. The reaction temperature is about −20 through about 150° C., and preferably about 20 through about 100° C. A temperature lower than this range can result in a slow reaction, whereas a temperature higher than this range is of no additional effect.

After the reaction, the reaction system is neutralized prior to removal of the solvent. Water is added to the reaction vessel after the removal of solvent, so as to allow crystallization of the reaction mixture. The precipitates obtained are filtered off, washed with water, and dried under reduced pressure to yield a bisphenol compound having a stilbene skeleton.

A bisphenol mixture of the present invention may be prepared by mixing two or more bisphenol compounds separately synthesized with one another, or separately synthesizing intermediates obtained in the middle of the manufacturing process of bisphenol compounds and mixing the intermediates prior to completion of the residual reaction.

The stilbene epoxy resin of the present invention is obtained through the known process of glycidyl etherification of the stilbene bisphenol given above. The known process makes the bisphenol react with an epihalohydrin in the presence of an alkali, such as sodium hydroxide. In order to give high-purity products, non-protic solvents and other solvents like dioxane are preferably used as disclosed in Japanese Patent Laid-open No. S-60-31517, the complete disclosure of which is incorporated herein by reference.

Suitable epihalohydrins useful in the epoxidation reaction include epichlorohydrin and epibromohydrin, although epichlorohydrin is preferred because of its availability and low material cost.

Preferred examples of the basic substance used in this reaction include, by way of example, alkali metal hydroxides like sodium hydroxide and potassium hydroxide. A preferred amount of basic substance used is an equivalent mole with respect to 1 mole of the phenolic hydroxyl group.

Using a lower amount of basic substance is desired. It results in the remaining hydrolytic chlorine. Lesser amounts of gel by-product are obtained which is advantageous from a manufacturing perspective. In contrast, using a greater amount of basic substance increases the amount of gel by-product and is therefore disadvantageous in the manufacturing process.

Solvents applicable to the reaction include, though not limited, non-protic polar solvents like dimethylsulfoxide, dimethylsulfone, dimethylformamide, dimethylacetamide, and tetramethylurea, and ethers like dioxane and tetrahydrofuran. A preferred amount of solvent is about 5 through about 60 parts by weight with respect to 100 parts by weight of epihalohydrin. An amount less than about 5 parts by weight does not exert the effects of the present invention, whereas a greater amount allows the intermolecular reaction to proceed which can lower the quality of the products.

The amount of epihalohydrin used is preferably about 2.5 through about 20 moles or more specifically about 4 through about 12 moles with respect to 1 mole of the phenolic hydroxyl group. The amount less than this range allows the intermolecular reaction to proceed, thereby lowering the quality of products, whereas the amount greater than this range lowers the yield and is disadvantageous from the industrial viewpoint.

The epoxidation reaction is implemented by dissolving or suspending the stilbene bisphenol derivative in a solution mixture of epihalohydrin and reaction solvent and further adding the basic substance to the solution with stirring. The reaction is generally carried out under reduced pressure. The reaction solution is subjected to an azeotropic process while the reaction temperature is kept in a range of about 30 to about 80° C. The volatile matter is condensed, the condensed solution thus obtained is subjected to an oil-water separation, the oil substance is returned to the reaction system, and the water is removed. The basic substance is added in limited amounts either separately or continuously over a period of about 2 through about 10 hours for the homogeneous reaction. Introducing the basic substance in one shot can cause the reaction to proceed locally and unfavorably gives a gel. After completion of the reaction, unreacted epihalohydrin and solvent are removed by distillation, and the residue is dissolved in a solvent separable from water, for example, methyl isobutyl ketone, for removal of insoluble inorganic salts. The solution is further washed with water to remove inorganic component(s) and the remaining polar solvent, and distilled to remove the remaining solvent to yield a final epoxy product.

The stilbene epoxy resin of the present invention may alternatively be obtained through simultaneous rearrangement reaction and epoxidation reaction of the 1,1-bis (hydroxyphenyl)-2-chloroethane derivative.

In this process, the preferable amount of the basic substance used is (an equivalent mole with respect to 1 mole of the phenolic hydroxyl group)+(an equivalent mole with respect to 1 mole of the hydrolytic chlorine). Since the 1,1-bis(hydroxyphenyl)-2-chloroethane derivative has two hydroxyl groups and one hydrolytic chlorine atom per molecule, three moles of the basic substance are preferably used with respect to 1 mole of the 1,1-bis(hydroxyphenyl)-2-chloroethane derivative. The less amount of basic substance results in the remaining hydrolytic chlorine, while giving a less amount of gel as a by-product and being thus advantageous in the manufacturing process. The greater amount of basic substance, on the other hand, increases the amount of gel and is thus disadvantageous in the manufacturing process. The essential conditions of epoxidation reaction are identical with those specified above.

A mixture of the epoxy resin represented by general formula (2) and that represented by general formula (4) according to the present invention may be prepared by mixing separately synthesized epoxy resins with one another, or separately synthesizing intermediates obtained in the middle of the epoxidation process and mixing the intermediates prior to completion of the residual epoxidation reaction.

In the process of synthesizing the stilbene phenol represented by general formula (1) as a material of epoxy resin, the stilbene phenol represented by general formula (3) is formed with the stilbene phenol of general formula (1). For example, a mixture of stilbene phenols having three different basic skeletons X—CH=CH—X, X—CH=CH—Y, and Y—CH=CH—Y are synthesized from two different phenols X and Y used as starting materials.

The stilbene epoxy resin represented by general formula (2) and having two different aryl groups bound to a carbon—carbon double bond is derived from the stilbene phenol of X—CH=CH—Y, where the benzene rings linked with the carbon—carbon double bond have different substituents at different positions. The epoxy resin according to the present invention is required to include the epoxy resin represented by general formula (2). The epoxy resin containing only that represented by general formula (2) is obtained by isolating X—CH=CH—Y from the mixture of stilbene phenols and glycidyl etherifying the stilbene phenol X—CH=CH—Y. An epoxy resin having a sufficiently low melting point and improved working properties can not be obtained by simply mixing epoxy resins derived from the stilbene phenols of X—CH=CH—X and Y—CH=CH—Y.

Combination of three or more phenols as starting materials gives a similar mixture of stilbene phenols. For example, three different phenols X, Y, and Z give a mixture of stilbene phenols having different basic skeletons of X—CH=CH—X, X—CH=CH—Y, X—CH=CH—Z, Y—CH=CH—Y, Y—CH=CH—Z, and Z—CH=CH—Z. The epoxy resin according to the present invention is required to include at least one of the epoxy resins derived from the stilbene phenols of X—CH=CH—Y, X—CH=CH—Z, and Y—CH=CH—Z. Staring materials of four or more phenols give similar mixtures.

The epoxy resin according to the present invention can include just one or more epoxy resins represented by general formula (2), or alternatively includes one or more epoxy resins represented by general formula (4) in addition to one or more epoxy resins represented by general formula (2). In a mixture of (A) one or a plurality of epoxy resins of general formula (2) and (B) one or a plurality of epoxy resins of general formula (4), the amount of the component (A) is generally not less than 1% by weight, or preferably not less than 10% by weight, with respect to the total weight of the components (A) and (B). The less content of the component (A) increases the melting point of the resulting epoxy resin and deteriorates the working properties in the mixing process with another component. The content of the component (A) is increased to give epoxy resins required to have a lower melting point and decreased to give epoxy resins required to have a higher melting point. In the process of the present invention, the component (A) and the component (B) may be synthesized separately and then mixed with each other.

The epoxy resin composition of the present invention may include the above stilbene epoxy resin together with another known epoxy resin. Known epoxy resins applicable for the epoxy resin composition include, for example, glycidyl ether compounds derived from divalent phenols, such as bisphenol A, bisphenol F, hydroquinone, resorcinol, dihydroxynaphthalene, bis(4-hydroxyphenyl) menthane, bis(4-hydroxyphenyl)dicyclopentane, 4,4'-dihydroxybenzophenone, bis(4-hydroxyphenyl) ether, bis(4-hydroxy-3-methylphenyl) ether, bis(3,5-di methyl-4-hydroxyphenyl) ether, bis(4-hydroxyphenyl) sulfide, bis(4-hydroxy-3-methylphenyl) sulfide, bis(3,5-dimethyl-4-hydroxyphenyl) sulfide, bis(4-hydroxyphenyl) sulfone, bis(4-hydroxy-3-methylphenyl) sulfone, bis(3,5-dimethyl4-hydroxyphenyl) sulfone, 1,1-bis(4-hydroxyphenyl) cyclohexane, 1,1-bis(4-hydroxy-3-methylphenyl) cyclohexane, 1,1-bis(3,5-dimethyl-4-hydroxyphenyl) cyclohexane, 4,4'-dihydroxybiphenyl, 4,4'-dihydroxy-3,3',5,5'-tetramethylbiphenyl, bis(hydroxynaphthyl)methane, 1,1'-binaphthol, and 1,1'-bis(3-t-butyl-6-methyl-4-hydroxyphenyl)butane; diglycidyl ether compounds derives from halogenated bisphenols, such as tetrabromobisphenol A; polyphenol and polynaphthol novolak resins obtained as reaction products of phenols, such as phenol, o-cresol, and catechol, or naphthols, such as hydroxynaphthalene and dihydroxynaphthalene, with aldehydes, such as formaldehyde; trityl skeleton-containing polyphenols obtained by condensation of phenols, such as phenol, cresol, and methyl-t-butylphenol, and aromatic aldehydes, such as hydroxybenzaldehyde; tritylskeleton-containing polyphenol novolaks obtained as reaction products of trityl skeleton-containing polyphenols with formaldehyde or the like; polyaralkylphenol resins and polyaralkylnaththol resins obtained as reaction products of phenols, such as phenol, o-cresol, and catechol, or naphthols, such as hydroxynaphthalene and dihydroxynaphthalene, with xylylene dichloride, bis(hydroxymethyl)benzene, or the like; alicyclic hydrocarbon-containing polyphenol resins and polynaththol resins obtained as reaction products of phenols, such as phenol, o-cresol, and catechol, or naphthols, such as hydroxynaphthalene and dihydroxynaphthalene, with unsaturated alicyclic hydrocarbons, such as dicyclopentadiene and limonene; alicyclic hydrocarbon-containing polyphenol novolak resins and polynaththol novolak resins obtained as reaction products of alicyclic hydrocarbon-containing polyphenol resins or polynaththol resins with formaldehyde or the like; glycidyl ether compounds of polyvalent phenols and polyvalent naththols obtained by condensation reaction of phenols or naththols with aromatic carbonyl compounds; glycidyl ether compounds derived from trivalent or higher multivalent phenols including as a fundamental skeleton fluoroglycine, tris(4-hydroxyphenyl)methane, 1,1,2,2,-tetrakis(4-hydroxyphenyl)ethane, 1,3-bis[bis(4-hydroxyphenyl) methyl]benzene, 1,4-bis[bis(4-hydroxyphenyl)methyl] benzene, or the like and cyclic phenols, such as calixarene.

The known epoxy resins also include amine epoxy resins derived from p-aminophenol, m-aminophenol, 4-amino-m-cresol, 6-amino-m-cresol, 4,4'-diaminodiphenylmethane, 3,3'-diaminodiphenylmethane, 4,4'-diaminodiphenyl ether, 3,4'-diaminodiphenyl ether, 1,4-bis(4-aminophenoxy) benzene, 1,4-bis(3-aminophenoxy)benzene, 1,3-bis(4-aminophenoxy)benzene, 1,3-bis(3-aminophenoxy)benzene, 2,2-bis(4-aminophenoxyphenyl)propane, p-phenylenediaminde, m-phenylenediaminde, 2,4-toluenediaminde, 2,6-toluenediamine, p-xylylenediamine, m-xylylenediamine, 1,4-cyclohexanebis(methylamine), 1,3-cyclohexanebis(methylamine), and N,N-diglycidylaniline; glycidyl ester compounds derived from aromatic carboxylic acids, such as p-oxybenzoic acid, m-oxybenzoic acid, terephthalic acid, and isophthalic acid; hydantoin epoxy compounds derived from 5,5-dimethylhydantoin or the like; alicyclic epoxy resins, such as 2,2-bis(3,4-epoxycyclohexyl) propane, 2,2-bis[4-(2,3-epoxypropyl)cyclohexyl]propane, vinylcyclohexene dioxide, 3,4-epoxycyclohexyl methyl-3, 4-epoxycyclohexane carboxylate; and aliphatic epoxy resins obtained by oxidation of the double bond included in unsaturated hydrocarbons, such as polybutadiene. One or a mixture of these epoxy resins may be included in the epoxy resin composition.

Suitable phenolic epoxy curing agents include, among others, polyphenol and polynaphthol novolak resins obtained as reaction products of phenols, such as phenol, o-cresol, and catechol, or naphthols, such as hydroxynaphthalene and dihydroxynaphthalene, with aldehydes, such as formaldehyde; tritylskeleton-containing polyphenols obtained by condensation of phenols, such as phenol, cresol, and methyl-t-butylphenol, and aromatic aldehydes, such as hydroxybenzaldehyde; tritylskeleton-containing polyphenol novolaks obtained as reaction products of tritylskeleton-containing polyphenols with formaldehyde or the like; polyaralkylphenol resins and polyaralkylnaththol resins obtained as reaction products of phenols, such as phenol, o-cresol, and catechol, or naphthols, such as hydroxynaphthalene and dihydroxynaphthalene, with xylylene dichloride, bis(hydroxymethyl)benzene, or the like; alicyclic hydrocarbon-containing polyphenol resins and polynaththol resins obtained as reaction products of phenols, such as phenol, o-cresol, and catechol, or naphthols, such as hydroxynaphthalene and dihydroxynaphthalene, with unsaturated alicyclic hydrocarbons, such as dicyclopentadiene and limonene; alicyclic hydrocarbon-containing polyphenol novolak resins and polynaththol novolak resins obtained as reaction products of alicyclic hydrocarbon-containing polyphenol resins or polynaththol resins with formaldehyde or the like; trivalent or higher multivalent phenols including as a fundamental skeleton fluoroglycine, tris(4-hydroxyphenyl)methane, 1,1,2,2-tetrakis(4-hydroxyphenyl) ethane, 1,3-bis[bis(4-hydroxyphenyl) methyl]benzene, 1,4-bis[bis(4-hydroxyphenyl)methyl]benzene, or the like; and cyclic phenols, such as calixarene. Preferred curing agents are phenol novolak resins, naphthol novolak resins, phenol aralkyl resins, naphthol aralkyl resins, tritylskeleton-containing polyphenols, tritylskeleton-containing polyphenol novolaks, alicyclic hydrocarbon-containing polyphenol resins, and alicyclic hydrocarbon-containing polynaththol resins because of their favorable curing properties and moisture resistance. The epoxy curing agent can comprise a single suitable compound or a mixture of suitable compounds.

In the curable epoxy resin composition, the phenolic epoxy curing agent (B) can, for instance, be comprised of a polyphenol resin having a melt viscosity of 1.5 poise or less at 150° C. An exemplary polyphenol resin can be represented by the general formula (5)

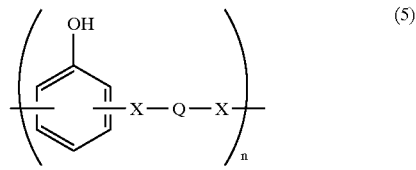

wherein X represents single bond or methylene, Q represents phenylene or a divalent alicyclic moiety derived from dicyclopentadiene or limonene, and n represents an integer of 1 to 20, preferably 1 to 10. The phenolic epoxy curing agent (B) can further comprise a phenol novolak. Exemplary divalent alicyclic moieties derived from dicyclopentadiene or limonene are specifically shown as below:

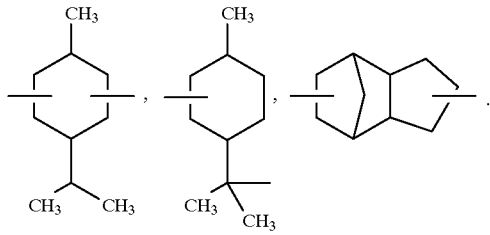

Divalent bisphenols may further be added according to the requirements. Examples of the applicable bisphenol include: divalent phenols, such as bisphenol A, bisphenol F, hydroquinone, resorcinol, dihydroxynaphthalene, bis(4-hydroxyphenyl)ethane, bis(4-hydroxyphenyl)propane, bis(4-hydroxyphenyl)butane, bis(4-hydroxyphenyl)pentane, bis(4-hydroxyphenyl)hexane, 1,3,3-trimethyl-1-m-hydroxyphenyl indan-5-or-7-ol, bis(4-hydroxyphenyl)menthane, bis(4-hydroxyphenyl)dicyclopentane, 4,4'-dihydroxybenzophenone, bis(4-hydroxyphenyl) ether, bis(4-hydroxy-3-methylphenyl) ether, bis(3,5-dimethyl-4-hydroxyphenyl) ether, bis(4-hydroxyphenyl) sulfide, bis(4-hydroxy-3-methylphenyl) sulfide, bis(3,5-dimethyl-4-hydroxyphenyl) sulfide, bis(4-hydroxyphenyl) sulfone, bis(4-hydroxy-3-methylphenyl) sulfone, bis(3,5-dimethyl-4-hydroxyphenyl) sulfone, 1,1-bis(4-hydroxyphenyl) cyclohexane, 1,1-bis(4-hydroxy-3-methylphenyl) cyclohexane, 1,1-bis(3,5-dimethyl-4-hydroxyphenyl) cyclohexane, 4,4'-dihydroxybiphenyl, 4,4-dihydroxy-3,3', 5,5 '-tetramethyl biphenyl, bis(hydroxynaphthyl)methane, 1,1'-binaphthol, and 1,1'-bis(3-t-butyl-6-methyl-4-hydroxyphenyl)butane; and halogenated bisphenols, such as tetrabromobisphenol A.

Other than the above phenols, the following compounds may also be added, depending on the application requirements, polycarboxylic acids, such as maleic acid, phthalic acid, nadic acid, methyl-tetrahydrophthalic acid, and methylnadic acid, and anhydrides thereof; polyamines, such as diaminodiphenylmethane, diaminodiphenylsulfone, diaminodiphenyl ether, phenylenediamine, diaminodicyclohexylmethane, xylylenediamine, toluenediamine, diaminocyclohexane, dichloro-diaminodiphenylmehtane (including their isomers), ethylenediamine, and hexamethylenediamine; and active hydrogen-containing compounds capable of reacting with the epoxy group, such as dicyandiamide and tetramethylguanidine. The content of the epoxy curing agent is preferably about 0.7 through about 1.2 times the weight of the epoxy resin, or more specifically an equivalent weight to that of the epoxy resin. An extreme shift from the equivalent composition results in lowering the moisture resistance and curing properties.

In the process of curing the epoxy resin composition of the present invention, a known curing accelerator may be added. Suitable applicable curing accelerators include, for instance, organophosphine compounds, such as triphenylphosphine, tri-4-methylphenylphosphine, tri-4-methoxyphenylphosphine, tributylphosphine, trioctylphosphine, and tri-2-cyanoethylphosphine, and their tetraphenylborates; tertiary amines, such as tributylamine, triethylamine, 1,8-diazabicyclo(5,4,0)-7-undecene, and triamylamine; quaternary ammonium salts, such as benzyltrimethylammonium chloride, benzyltrimethylammonium hydroxide, and triethylammonium tetraphenylborate; andimidazoles. Because of their favorable moisture resistance and curing properties, organophosphine compounds, 1,8-diazabicyclo(5,4,0)-7-undecene, andimidazoles, especially triphenylphosphine, are preferred.

The epoxy resin compositions according to the present invention can further comprise, optionally, inorganic fillers as a component (C). Suitable inorganic fillers include, for instance, silica, alumina, titanium white, aluminum hydroxide, talc, clay, or glass fibers. Silica and alumina are particularly preferred examples. The inorganic fillers used may be a bulky mixture of different shapes (spherical and ground) and sizes. The content of inorganic fillers is required to be about 25 through about 95% by weight with respect to the total weight of the resin composition, and is preferably about 70 through about 95% by weight, although most preferably it is about 80 through about 95% by weight. The content of inorganic fillers less than about 80% by weight results in poor moisture resistance, whereas that greater than about 95% by weight deteriorates the molding properties.

The spherical powder may be approximately spheres in shape possessing no acute vertices and having the aspect ratio of about 1.0 through about 1.2. Preferably used is spherical powder having the spherical degree similar to that of commercially available silica powder prepared by flame spraying or sol-gel method, where that substantially close to the true sphere is especially preferable. When the standard spherical process is not applicable, spherical powder may be prepared by making finely ground particles mixed with a binder spherical by a mechanochemical approach.

The ground particles may be polyhedrons or bodies of any other irregular shapes possessing vertices. Ground particles of non-crystalline or crystalline quartz obtained by grinding synthetic or natural quartz block are preferable; for example, ground molten silica.

Although any spherical powder is applicable to the present invention, a preferred example including three components x, y, and z is described as follows. The x, y, and z components respectively have the average particle diameter of not less than about 0.1 $\mu$m and not greater than about 1.5 $\mu$m, not less than about 2 $\mu$m and not greater than about 15 $\mu$m, and not less than about 20 $\mu$m and not greater than about 70 $\mu$m, or more preferably having the average particle diameter of not less than about 0.1 μm and not greater than about 1.0 μm, not less than about 2 μm and not greater than about 10 μm, and not less than about 20 μm and not greater than about 50 μm. Powder having the average particles diameter of less than about 0.1 μm causes aggregation of particles, which interferes with homogeneous dispersion into the resin composition and may damage the flow properties. On the other hand, powder having the average particle diameter of greater than about 70 μm can not be easily charged into the fine portions of semiconductor elements. The x, y, and z components having the average particle diameter out of the respective ranges deteriorate the flow properties of the resin composition. The spherical powder used in the present invention preferably has a narrower variance of particle diameter, or more specifically a single variance. Therefore using a classification process is preferred in order to select particles having substantially uniform particle diameters for all the x, y, and z components. The average particle diameter here is defined as the particle diameter value under the condition of about 50% weight cumulation when the distribution of particle diameter is measured with a particle size distribution measuring apparatus, for example, a laser scattering granulometer.

The volume ratios of the spherical powdery components x, y, and z with respect to the calculated total volume of the x, y, and z components are preferably not less than about 10% by volume and not greater than about 24% by volume, not less than about 0.1% by volume and not greater than about 66% by volume, and not less than about 24% by volume and not greater than about 76% by volume, more preferably not less than about 10% by volume and not greater than about 24% by volume, not less than about 0.1% by volume and not greater than about 36% by volume, and not less than about 57% by volume and not greater than about 76% by volume, or most preferably not less than about 10% by volume and not greater than about 20% by volume, not less than about 4% by volume and not greater than about 30% by volume, and not less than about 60% by volume and not greater than about 76% by volume. The volume ratios out of these ranges lower the flow properties of the resulting resin composition.

The values of '% by volume' in the present invention are calculated using the quotients obtained by dividing the respective weights of the x, y, and z components by their true specific gravities as volumes of the respective components.

In general, the apparent volume of particles having a certain particle diameter distribution is varied by the filling conditions of particles in a measuring vessel and before and after the process of mixing different sets of particles. In the description above, the apparent volume is thus not used for the calculation of '% by volume' of each component or set of particles.

The ground particles (component m) used in the present invention have an average particle diameter of not less than about 1 μm and not greater than about 70 μm, or preferably not less than about 1 μm and not greater than about 30 μm. A preferred ratio of the weight of the ground particles (component m) to the total weight of the component of spherical powder and the component m of ground particles is not less than about 1% by weight and not greater than about 30% by weight. The content less than this range does not have sufficient effects of reducing fins and flashes (thin resin films formed by the leaked resin substance) formed according to the properties of resin and the shapes of the encapsulating device and molding device used. The content exceeding this range, on the other hand, lowers the flow properties of the resulting resin composition.

It is preferable that the fillers used in the present invention are sufficiently mixed and blended in advance. According to a concrete procedure, the fillers are blended with a device utilizing rotors or the air, such as a mixer or a Ko-kneader, or a device for vibrating, shaking, or rotating a vessel with the fillers set therein. In order to determine whether the fillers are sufficiently kneaded, particle size distributions are measured for samples from different positions and compared with one another for identification. The fillers may be pre-treated with a coupling agent or resin according to the requirements. One applicable method of pre-treatment mixes a coupling agent or resin with the fillers in a solvent and subsequently removes the solvent. Another method directly mixes a coupling agent or resin with the fillers by means of a blender.

Natural wax, synthetic wax, higher fatty acids and their metal salts, parting agents like paraffin, coloring agents like carbon black, and finishing agents like silane coupling agents may further be added to the composition of the present invention. Flame-retardants, such as fillers like antimony trioxide, or phosphorus compounds or brominated epoxy resins, may also be added. Brominated epoxy resins are especially preferable for obtaining flame-retarding effects.

A variety of non-reacted or reacted elastomers may be added in order to lower the stress. Suitable non-reacted or reacted elastomers include, for instance, polybutadiene, butadiene-acrylonitrile copolymer, silicone rubber, and silicone oil.

Resin compositions according to the present invention can be used for encapsulating semi-conductors or other electronic parts. the resultant resin-encapsulated semiconductor devices are prepared using a known molding process, such as transfer molding, compression molding, or injection molding.

Resin compositions according to the present invention are described in Japanese Application 07-108418 filed May 2, 1995, Japanese Application 07-106769 filed Apr. 28, 1995, Japanese Application 07-106768 filed Apr. 28, 1995, and Japanese Application 07-104464 filed Apr. 27, 1995, the complete disclosures of which are incorporated herein by reference.

EXAMPLES

Examples of the present invention are given below, although the invention is not restricted in any sense to these examples.

In the description below, the epoxy equivalent weight is defined by the molecular weight of epoxy resin per epoxy group.

The quantity of hydrolytic chlorine expressed by ppm was measured by dissolving the epoxy resin in dioxane, adding an alcohol solution of potassium hydroxide to the resin solution, heating the resin solution for 30 minutes under reflux, and measuring the quantity of chlorine ions released from the resin solution by back titration with an aqueous solution of silver nitrate.

Properties of the kneaded substances and cured objects were evaluated according to the following methods.

* Working properties: The working properties in the mixing process of kneading the resin component, inorganic fillers, and other additives were evaluated using Reference 3 as a standard. Open circles (o) represent equivalent working properties to those of Reference 3 and crosses (x) represent poor working properties having difficulty in preparation of homogeneous material.

* Barcol hardness: The Barcol hardness was measured under the condition of 175° C./90 sec with a model-935 hardness tester according to ASTM D-648.

* Glass transition temperature: The glass transition temperature was measured with a heat mechanical analyzer (SHIMADZU DT-30).

* Bending strength, Bending modulus: The bending strength and the bending modulus were measured with a tensile machine (SHIMADZU IS-10T) according to JIS K-6911.

* Water absorption: The variation in weight was measured under the condition of 85° C./85% RH with a constant-temperature, constant-humidity bath (Advantec TOYO AGX-326).

* Spiral flow: The spiral flow was measured under the condition of 175° C./70 kg/cm2 in conformity with EMMI-1-66.

* Solder cracking: Simulated ICs (52-pin QFD packaging: thickness in packaging=2.05 mm) were exposed to the moisture under the condition of 85° C./85% RH and then soaked in a solder bath of 240° C. for 30 seconds. The number of ICs having cracks were measured. Ten samples were tested for each resin.

Reference 1

(1) Synthesis of 1,1-bis(hydroxyphenyl)-2-chloroethane derivative-1

In a 2-liter four-necked flask with a thermometer, a stirrer, and a condenser, 244.4 g (2.0 mol) of 2,6-xylenol (hereinafter referred to as 26XY) and 193.8 g (1.0 mol) of a 40.5% aqueous solution of chloroacetaldehyde were added to and dissolved in 376 g of acetic acid with stirring, and the reaction solution was then cooled to 5° C. A solution prepared by mixing 122 g (1.2 mol) of concentrated sulfuric acid with 84 g of acetic acid was added dropwise to the reaction mixture at 5° C. over 3 hours. The reaction mixture was then maintained at the constant temperature of 25° C. for 6 hours, and stirred overnight at ambient temperature. The reaction mixture was again cooled to 5° C., and deposited precipitates were filtered off. The precipitates thus obtained were washed with 500 g of water six times and dried in vacuo at 40° C. for 8 hours to give 264 g of colorless precipitates (yield: 86.6%) (hereinafter referred to as XYCE). Gel permeation chromatography (hereinafter referred to as GPC: detected with the ultraviolet ray of 254 nm) showed that the purity of the product was 98.3%, while infrared absorption spectrum gave a broad absorption band due to the hydroxyl group in the vicinity of 3500 cm−1. A fragment of the molecular weight=304 was observed by mass spectrometry.

(2) Synthesis of stilbene bisphenol-1

In a 2-liter ((liter)) four-necked flask with a thermometer, a stirrer, and a condenser, 225.6 g of XYCE obtained in the above process (1) was dissolved with stirring in 451.2 g of methanol under nitrogen atmosphere. After 91.9 g of a 48.3% aqueous solution of sodium hydroxide was added dropwise to the solution over 1 hour at the internal temperature of 30° C., the reaction mixture was heated and reacted for 3 hours under reflux of methanol. After the reaction, complete disappearance of the material XYCE was confirmed by high performance liquid, chromatography (hereinafter referred to as LC). The reaction mixture was cooled to 60° C. and neutralized with 37.5 g of concentrated hydrochloric acid. After removal of methanol, 1000 g of warm water was added to the reaction mixture, and precipitates thus deposited were filtered off. The precipitates obtained were washed with water and dried in vacuo at 80° C. for 8 hours to give 192 g of yellow precipitates (yield: 96.7%) (hereinafter referred to as XYSB). GPC showed that the purity of the product was 98.1%, while infrared absorption spectrum gave a broad absorption band due to the hydroxyl group in the vicinity of 3400 cm−1. A fragment of the molecular weight (mw=268) was observed by mass spectrometry.

(3) Synthesis of epoxy resin-1

In a reaction vessel with a thermometer, a stirrer, a dropping funnel, and a columned condenser, 100 g of the material phenol (XYSB) obtained in the above process (2) was dissolved in 485.6 g of epichlorohydrin and 242.8 g of 1,4-dioxane. While the reaction system was kept at 140 torr, 61.71 g of a 48.3% aqueous solution of sodium hydroxide was continuously added dropwise over 5 hours at the temperature of 62° C. The reaction proceeded at the fixed temperature of 62° C., while the azeotropic mixture of epichlorohydrin and water was cooled and liquefied and the organic phase was returned to the reaction system.

After completion of the reaction, unreacted epichlorohydrin and 1,4-dioxane were removed by evaporation under reduced pressure. The glycidyl ether obtained and by-product salts were dissolved in 800 g of methyl isobutyl ketone and washed with water for removal of the by-product salts. Subsequent removal of methyl isobutyl ketone at 160° C. under the reduced pressure of 10 torr gave 122.2 g of final product (yield: 86.2%) (hereinafter referred to as XYCC-E).

The product had the purity of 93.0% measured by GPC (detected with a differential refractometer), the melting point of 151° C., and the epoxy equivalent weight of 198 g/eq. Infrared spectroscopy showed that the absorption due to the phenolic hydroxyl group disappeared and that the product had absorptions of 1240 cm−1 and 915 cm−1 due to the epoxy group.

Reference 2

(1) Synthesis of 1,1-bis(hydroxyphenyl)-2-chloroethane derivative-2

Synthesis was carried out in the same manner as Reference 1 (1), except that 328.5 g (2.0 mol) of 3-methyl-6-t-butylphenol (hereinafter referred to as 3M6B) was used in place of 244.4 g (2.0 mol) of 26XY, to gave 317 g of pale purple precipitates (yield: 81.5%) (hereinafter referred to as XMCE-100). GPC (detected with the ultraviolet ray of 254 nm) showed that the purity of the product was 87.7%, while infrared absorption spectrum gave a broad absorption band due to the hydroxyl group in the vicinity of 3500 cm−1. A fragment of the molecular weight=389 was observed by mass spectrometry.

(2) Synthesis of stilbene bisphenol-2

Synthesis was carried out in the same manner as Reference 1(2), except that XMCE-100 obtained in the above process (1) of Reference 2 was used in place of XYCE, to gave 134 g of pale yellow precipitates (yield: 94.8%) (hereinafter referred to as XMSB-100). GPC showed that the purity of the product was 93.5%, while infrared absorption spectrum gave a broad absorption band due to the hydroxyl group in the vicinity of 3100 cm−1. A fragment of the molecular weight=352 was observed by mass spectrometry.

(3) Synthesis of epoxy resin-2

The epoxidation was carried out in the same manner as Reference 1(3), except that XMSB-100 obtained in the above process (2) was used in place of XYSB, to gave 54.7 g of final product (yield: 36.2%) (hereinafter referred to as XMCC-100E). The product had the purity of 95.2% measured by GPC (detected with a differential refractometer), the melting point of 220 through 224° C., and the epoxy equivalent weight of 230 g/eq. Infrared spectroscopy showed that the absorption due to the phenolic hydroxyl group disappeared and that the product had absorptions of 1230 cm−1 and 920 cm−1 due to the epoxy group.

Example 1 (1)

(1) Synthesis of 1,1-bis(hydroxyphenyl)-2-chloroethane derivative-3

Synthesis was carried out in the same manner as Reference 1 (1), except that 195.5 g (1.6 mol) of 26XY and 65.7 g (0.4 mol) of 3M6B were used in place of 244.4 g (2.0 mol) of 26XY, to gave 271 g of pale purple precipitates (yield: 84.1%) (hereinafter referred to as XMCE-20). GPC (detected with the ultraviolet ray of 254 nm) showed that the purity of the product was 97.7%, while infrared absorption spectrum gave broad absorption bands due to the hydroxyl group in the vicinity of 3450 cm−1 and 3550 cm−1. Fragments of the molecular weight=346 and 304 were observed by mass spectrometry. XMCE-100 of Reference 2(1) ((Reference 4)) was not observed by LC analysis.

(2) Synthesis of stilbene bisphenol-3

Synthesis was carried out in the same manner as Reference 1(2), except that 144.8 g of XMCE-20 obtained in the above process (1) of Example 1 was used in place of XYCE; to gave 124 g of yellow precipitates (yield: 96.6%) (hereinafter referred to as XMSB-20). GPC (detected with the ultraviolet ray of 254 nm) showed that the purity of the product was 97.1%, while infrared absorption spectrum gave a broad absorption band due to the hydroxyl group in the vicinity of 3400 cm−1. Fragments of the molecular weight= 310 and 268 were observed by mass spectrometry. XMSB-100 of Reference 2(2) ((Reference 5)) was not observed by LC analysis.

(3) Synthesis of epoxy resin -3

The epoxidation was carried out in the same manner as Reference 1(3), except that 99.7 g of XMSB-20 obtained in the above process (2) was used in place of XYSB, to gave 131 g of final product (yield: 94%) (hereinafter referred to as XMCC-20E).

GPC (detected with a differential refractometer) showed that the purity of the product was 93.6% and the rate of the stilbene epoxy compound including the 26XY residue and the 3M6B residue ((including 26XY and 3M6B)) in its molecular structure was 39.6%. The product had the melting point of 110 through 130° C., and the epoxy equivalent weight of 208 g/eq. Infrared spectroscopy showed that the absorption due to the phenolic hydroxyl group disappeared and that the product had absorptions of 1240 cm−1 and 920 cm−1 due to the epoxy group.

Example 2

(1) Synthesis of 1 1-bis(hydroxyphenyl)-2-chloroethane derivative-4

Synthesis was carried out in the same manner as Reference 1(1), except that 171.1 g (1.4 mol) of 26XY and 98.6 g (0.6 mol) of 3M6B were used in place of 244.4 g (2.0 mol) of 26XY, to gave 253g of pale purple precipitates (yield: 76.7%) (hereinafter referred to as XMCE-30). GPC (detected with the ultraviolet ray of 254 nm) showed that the purity of the product was 96.0%, while infrared absorption spectrum gave broad absorption bands due to the hydroxyl group in the vicinity of 3450 cm−1 and 3550 cm−1. Fragments of the molecular weight=346 and 304 were observed by mass spectrometry. XMCE-100 of Reference 2(1) ((Reference 4)) was not observed by LC analysis.

(2) Synthesis of stilbene bisphenol-

Synthesis was carried out in the same manner as Reference 1(2), except that 122.1 g of XMCE-30 obtained in the above process (1) was used in place of XYCE, to gave 108 g of yellow precipitates (yield: 99.4%) (hereinafter referred to as XMSB-30). GPC (detected with the ultraviolet ray of 254 nm) showed that the purity of the product was 93.3%, while infrared absorption spectrum gave a broad absorption band due to the hydroxyl group in the vicinity of 3400 cm−1. Fragments of the molecular weight=310 and 268 were observed by mass spectrometry. XMSB-100 of Reference 2(2) was not observed by LC analysis.

(3) Synthesis of epoxy resin-4

The epoxidation was carried out in the same manner as Reference 1(3), except that 95.4 g of XMSB-30 obtained in the above process (2) was used in place of XYSB, to gave 118 g of final product (yield: 89.5%) (hereinafter referred to as XMCC-30E).

GPC (detected with a differential refractometer) showed that the purity of the product was 86.6% and the rate of the stilbene epoxy compound including the 26XY residue and the 3M6B residue ((including 26XY and 3M6B)) in its molecular structure was 53.2%. The product was semisolid at ambient temperature and had the epoxy equivalent weight of 200 g/eq. The melt viscosity was 0.16 poise at 150° C. Infrared spectroscopy showed that the absorption due to the phenolic hydroxyl group disappeared and that the product had absorptions of 1260 cm−1 and 910 cm−1 due to the epoxy group.

Example 3

(1) Synthesis of 1,1-bis(hydroxyphenyl)-2-chloroethane derivative-5

Synthesis was carried out in the same manner as Reference 1(1), except that 122.2 g (1.0 mol) of 26XY and 164.3g (1.0 mol) of 3M6B were used in place of 244.4 g (2.0 mol) of 26XY, to gave 321 g of colorless precipitates (yield: 92.5%) (hereinafter referred to as XMCE-50). GPC (detected with the ultraviolet ray of 254 nm) showed that the purity of the product was 90.7%, while infrared absorption spectrum gave broad absorption bands due to the hydroxyl group in the vicinity of 3450 cm−1 and 3550 cm−1. Fragments of the molecular weight=346 and 304 and a faint fragment of the molecular weight=389 were observed by mass spectrometry.

(2) Synthesis of stilbene bisphenol-

Synthesis was carried out in the same manner as Reference 1(2), except that 114.7 g of XMCE-50 obtained in the above process (1) was used in place of XYCE, to gave 98.5 g of pale brown precipitates (yield: 95.8%) (hereinafter referred to as XMSB-50). GPC (detected with the ultraviolet ray of 254 nm) showed that the purity of the product was 96.5% and the rate of the stilbene compound including the 26XY residue and the 3M6B residue ((including 26XY and 3M6B)) in its molecular structure was 86.4%. Infrared absorption spectrum gave a broad absorption band due to the hydroxyl group in the vicinity of 3400 cm−1. Fragments of the molecular weight=310 and 268 and a faint fragment of the molecular weight (mw=352) were observed by mass spectrometry. (3) Purification of stilbene bisphenol XMSB-50 obtained in the above process (2) of Example 3 was recrystallized from toluene. Precipitates thus obtained were washed with cyclohexane and dried under reduced pressure to yield fine brown precipitates. The purity measured by high performance liquid chromatography (hereinafter referred to as LC) was 99.1%, and the retention time of the fine precipitates measured by LC completely coincided with the retention time of the stilbene bisphenol including the 26XY residue and the 3M6B residue ((including 26XY and 3M6B)) in its molecular structure, which was obtained in the process (2) of Example 3. Infrared absorption spectrum gave a broad absorption band due to the hydroxyl group in the vicinity of 3500 cm−1. A fragment of the molecular weight= 310 was observed by mass spectrometry.

* Melting point: 175 through 179° C.
* 1H-NMR &D: 1.43ppm (s, t-butyl group, 9H)

2.27 ppm (s, Ar—CH3, 6H)

2.33 ppm (s, Ar—CH3, 3H)

4.77 ppm (brs, hydroxyl group, 2H)

6.5–7.5 ppm (m, Ar—H, —CH=CH—, 6H)

(4) Synthesis of epoxy resin-5

The epoxidation was carried out in the same manner as Reference 1(3), except that 99.7 g of XMSB-50 obtained in the above process (2) was used in place of XYSB, to gave 131 g of final product (yield: 94%) (hereinafter referred to as XMCC-50E). GPC (detected with a differential refractometer) showed that the purity of the product was 93.5% and the rate of the stilbene epoxy compound including the 26XY residue and the 3M6B residue in its molecular structure was 80.5%. The product had the melting point of 45° C., the epoxy equivalent weight of 226 g/eq, and the melt viscosity of 0.2 poise at 150° C. Infrared spectroscopy showed that the absorption due to the phenolic hydroxyl group disappeared and that the product had absorptions of 1260 cm−1 and 920 cm−1 due to the epoxy group.

(5) Synthesis of epoxy resin-6

The epoxidation was carried out in the same manner as Reference 1(3), except that 38.8 g of the recrystallized product obtained in the above process (3) of Example 3 was used in place of XYSB, to gave 50.2 g of pale yellow viscous liquid substance (yield: 95%). The purity measured by LC was 94.2% for the stilbene epoxy compound including the 26XY residue and the 3M6B residue ((including 26XY and 3M6B)) in its molecular structure. Infrared spectroscopy showed that the absorption due to the phenolic hydroxyl group disappeared and that the product had absorptions of 1260 cm−1 and 910 cm−1 due to the epoxy group. *1H-NMR &D: 1.42 ppm (s, t-butyl group, 9H)

2.32 ppm (s, Ar—CH3, 6H)

2.38 ppm (s, Ar—CH3, 3H)

2.7–3.0 ppm (m, epoxy-CH2, 4H)

3.4 ppm (m, epoxy-CH, 2H)

3.7–4.3ppm (m, —OCH2, 4H)

6.6–7.5 ppm (m, Ar—H, —CH=CH—, 6H)

Example 4

(1) Synthesis of 1,1-bis(hydroxyphenyl)-2-chloroethane derivative-6

Synthesis was carried out in the same manner as Reference 1(1), except that 91.7 g (0.75 mol) of 26XY and 205.4 g ((164.3g)) (1.25 mol) of 3M6B were used in place of 244.4 g (2.0 mol) of 26XY, to gave 315 g of pale purple precipitates (yield: 88.0%) (hereinafter referred to as XMCE-62.5). GPC (detected with the ultraviolet ray of 254 nm) showed that the purity of the product was 94.4%, while infrared absorption spectrum gave broad absorption bands due to the hydroxyl group in the vicinity of 3450 cm−1 and 3550 cm−1. Fragments of the molecular weight=346, 389, and 304 were observed by mass spectrometry.

(2) Synthesis of stilbene bisphenol-6

Synthesis was carried out in the same manner as Reference 1(2), except that 121.1 g of XMCE-62.5 obtained in the above process (1) was used in place of XYCE, to gave 103 g of pale brown precipitates (yield: 94.7%) (hereinafter referred to as XMSB-62.5). GPC (detected with the ultraviolet ray of 254 nm) showed that the purity of the product was 92.0%, while infrared absorption spectrum gave a broad absorption band due to the hydroxyl group in the vicinity of 3500 cm−1. Fragments of the molecular weight (mw=310, 268, and 352) were observed by mass spectrometry.

(3) Synthesis of epoxy resin-7

The epoxidation was carried out in the same manner as Reference 1(3), except that 80.3 g of XMSB-62.5 obtained in the above process (2) of Example 4 was used in place of XYSB, to gave 95.2 g of final product (yield: 87.9%) (hereinafter referred to as XMCC-62.5E). GPC (detected with a differential refractometer) showed that the purity of the product was 85.8% and the rate of the stilbene epoxy compound including the 26XY residue and the 3M6B residue ((including 26XY and 3M6B)) in its molecular structure was 71.0%. The product had the melting point of 105 through 125° C., the epoxy equivalent weight of 230 g/eq, and the melt viscosity of 0.4 poise at 150° C. Infrared spectroscopy showed that the absorption due to the phenolic hydroxyl group disappeared and that the product had absorptions of 1260 cm−1 and 915 cm−1 due to the epoxy group.

Example 5

This Example concerns a test for the solubility of epoxy resins in solvent.

Solubility of the epoxy resins obtained in Examples 1, 2, 3, and 4 and References 1 and 2 (XMCC-20E, XMCC-30E, XMCC-50E, XMCC-62.5E, XMCC-100E, XYCC-E) was measured by adding 80 parts by weight of methyl isobutyl ketone to 20 parts by weight of each epoxy resin and heating each solution to 80° C. As for the epoxy resins obtained in References 1 and 2, solubility was also measured when 10 parts by weight of each epoxy resin was mixed with 80 parts by weight of methyl isobutyl ketone.

The results of measurement are shown in Table 1where open circles and crosses represent 'dissolved' and 'not dissolved', respectively. Melting points of the respective epoxy resins are also given in Table 1.

TABLE 1

| Epoxy Resins | Melting Point | Solubility |
| --- | --- | --- |
| XMCC-20E | 110–130° C. | o |
| XMCC-30E | Semisolid at room temperature | o |
| XMCC-50E | 45° C. | o |
| XMCC-62.5E | 105–125° C. | o |
| XMCC-100E | 220–224° C. | x |
| XYCC-E | 151° C. | x |
| XMCC-100E/XYCC-E | 151–160° C. | x |

Reference 3

(1) Synthesis of 1,1-bis(hydroxyphenyl)-2-chloroethane derivative-7

In a 2-liter four-necked flask with a thermometer, a stirrer, and a condenser, 244.4 g (2.0 mol) of 2,6-xylenol (hereinafter referred to as 26XY) and 124.5 g (1.0 mol) of chloroacetaldehyde dimethylacetal were added to and dissolved in 376 g of acetic acid with stirring, and the reaction solution was then cooled to 5° C. A solution prepared by mixing 122 g (1.2 mol) of concentrated sulfuric acid with 84 g of acetic acid was added dropwise to the reaction solution at 10° C. over 3 hours. The reaction system was then maintained at the constant temperature of 25° C. for 6 hours, and stirred overnight at ambient temperature. The reaction system was again cooled to 5° C., and deposited precipitates were filtered off. The precipitates thus obtained were washed with 500 g of water six times and dried in vacuo at 40° C. for 8 hours to give 268 g of pale purple precipitates.

(2) Synthesis of stilbene bisphenol-7

After 245.2 g of an 48.3% aqueous solution of sodium hydroxide and 552 g of N-methylpyrrolidone were placed in a 2-liter four-necked flask with a thermometer, a stirrer, and a condenser, the atmosphere in the flask was replaced with nitrogen. The solution was heated to 140° C. under the nitrogen encapsulating condition. A solution mixture prepared by mixing 225.6 g of the phenol intermediate obtained in the above process (1) of Reference 3((Reference 3)) with 676 g of N-methylpyrrolidone was added dropwise to the heated solution at 140° C. over 1.5 hours and maintained at the same temperature for 2 hours. The reaction system was cooled to 60° C. and neutralized with 226 g of concentrated hydrochloric acid. After removal of the solvent under reduced pressure, 1000 g of ion-exchanged water was added to the reaction mixture, and precipitates thus deposited were filtered off. The precipitates obtained were washed with ion-exchanged water three times and dried in vacuo at 80° C. for 8 hours to give 190 g of yellow precipitates.

(3) Synthesis of epoxy resin-8

In a reaction vessel with a thermometer, a stirrer, a dropping funnel, and a columned condenser, 100 g of the material phenol obtained in the above process (2) of Reference 3((Reference 3)) was dissolved in 485.6 g of epichlorohydrin and 243.1 g of dimethyl sulfoxide. While the reaction system was kept at 43 torr, 61.71 g of a 48.3% aqueous solution of sodium hydroxide was continuously added dropwise over 5 hours at the temperature of 48° C. The reaction proceeded at the fixed temperature of 48° C., while the azeotropic mixture of epichlorohydrin and water was cooled and liquefied and the organic phase was returned to the reaction system.

After completion of the reaction, unreacted epichlorohydrin was removed by evaporation under reduced pressure. By-product salts and the glycidyl ether including dimethylsulfoxide thus obtained were dissolved in 644 g of methyl isobutyl ketone and washed with water for removal of the by-product salts and dimethylsulfoxide. Subsequent removal of methyl isobutyl ketone at 160° C. under the reduced pressure of 10 torr gave a final product (hereinafter referred to as XYCC-E). The product had the melting point of 151° C., the epoxy equivalent weight of 198 g/eq, and the hydrolytic chlorine of 170 ppm.

Example 6 Synthesis of epoxy resin-9

An intermediate and then a material phenol were obtained in the same manner as Reference 3, except that 195.5 g (1.6 mol) of 26XY and 65.7 g (0.4 mol) of 3M6B were used in place of 244.4 g (2.0 mol) of 26XY, and the material phenol was epoxidized according to the process of Reference 3 to yield a final product (hereinafter referred to as XMCC-20E).

The product had the melting point of 110 to 130° C., the epoxy equivalent weight of 208 g/eq, and the hydrolytic chlorine of 170 ppm. The melt viscosity was 0.1 poise at 150° C.

Example 7 Synthesis of epoxy resin-10

An intermediate and then a material phenol were obtained in the same manner as Reference 3, except that 171.1 g (1.4 mol) of 26XY and 98.6 g (0.6 mol) of 3M6B were used in place of 244.4 g (2.0 mol) of 26XY, and the material phenol was epoxidized according to the process of Reference 3 to yield a final product (hereinafter referred to as XMCC-30E).

The product was semisolid at room temperature and had the epoxy equivalent weight of 200 g/eq and the hydrolytic chlorine of 190 ppm. The melt viscosity was 0.16 poise at 150° C.

Example 8 Synthesis of epoxy resin-11

An intermediate and then a material phenol were obtained in the same manner as Reference 3, except that 122.2 g (1.0 mol) of 26XY and 164.3 g (1.0 mol) of 3M6B were used in place of 244.4 g (2.0 mol) of 26XY, and the material phenol was epoxidized according to the process of Reference 3((Reference 4)) to yield a final product (hereinafter referred to as XMCC-50E).

The product had the melting point of 45° C., the epoxy equivalent weight of 226 g/eq, and the hydrolytic chlorine of 170 ppm. The melt viscosity was 0.2 poise at 150° C.

Example 9 Synthesis of epoxy resin-12

An intermediate and then a material phenol were obtained in the same manner as Reference 3, except that 91.7 g (0.75 mol) of 26XY and 205.4 g ((164.3g)) (1.25 mol) of 3M6B were used in place of 244.4 g (2.0 mol) of 26XY, and the material phenol was epoxidized according to the process of Reference 3 ((Reference 4)) to yield a final product (hereinafter referred to as XMCC-62.5E). The product had the melting point of 105 to 125° C., the epoxy equivalent weight of 230 g/eq, and the hydrolytic chlorine of 180 ppm. The melt viscosity was 0.4 poise at 150° C.

Example 10 Synthesis of epoxy resin-13

An intermediate and then a material phenol were obtained in the same manner as Reference 3, except that 328.5 g (2.0 mol) of 3M6B was used in place of 244.4 g (2.0 mol) of 26XY, and the material phenol was epoxidized according to the process of Reference 3 ((Reference 4)) to yield a final product (hereinafter referred to as XMCC-100E).

The product had the melting point of 220 to 224° C., the epoxy equivalent weight of 230 g/eq, and the hydrolytic chlorine of 130 ppm. ((hereinafter referred to as XMCC-100E)).

Examples 11–14 and Controls 1–3

Each of the glycidyl ethers obtained in Reference 3 and Examples 6 through 10 ((References 6 through 10)) or a commercially available glycidyl ether of 4,4'-dihydroxy-3, 3',5,5'-tetramethylbiphenyl (manufactured by SUMITOMO CHEMICAL CO., LTD.) was mixed with phenol novolak (trade name: Tamanol 758 manufactured by Arakawa Chemical Industries Co., Ltd.) working as a curing agent, triphenylphosphine working as a curing accelerator, molten silica (the grade and composition are shown below) as fillers, and carnauba wax and a coupling agent (trade name: SH-6040 manufactured by Toray Dowcorning Silicone Co., Ltd.) as mold parting agents, according to the composition (g) shown in Table 2. Each composition was subjected to milling under application of heat and subsequently to transfer molding.

Cured objects were obtained after the 5-hour post curing process in a 180° C. oven. Physical properties of the cured objects were measured. The results of measurement are shown in Table 2. Grade and composition of molten silica.

1. FS-20: ground silica (average particle diameter: 5.6 m) by DENKI KAKAGU KOGYO K.K.

2. Admafine SO-C2: spherical silica (average particle diameter: 0.4 m) by Admatec Co., Ltd.

3. Silstar MK-06: spherical silica (average particle diameter: 4.9 m) by Nippon Chemical Industrial Co., Ltd.

4. Excelica SE-40: spherical silica (average particle diameter: 40.4 m) by Tokuyama Corp.

A mixture containing 10% by weight of silica 1, 10.8% by weight of silica 2, 18% by weight of silica 3, and 61.2% by weight by silica 4 was used as fillers in Table 2.

TABLE 2

|  |  | Example 11 | Example 12 | Example 13 | Example 14 | Control 1 | Control 2 | Control 3 |
|---|---|---|---|---|---|---|---|---|
| Composition (parts by wt) | | | | | | | | |
| XMCC-20E |  | 100 | — | — | — | — | — | — |
| XMCC-30E |  | — | 100 | — | — | — | — | — |
| XMCC-50E |  | — | — | 100 | — | — | — | — |
| XMCC-62.5E |  | — | — | — | 100 | — | — | — |
| XYCC-E |  | — | — | — | — | 100 | — | — |
| XMCC-100E |  | — | — | — | — | — | 100 | — |
| Biphenyl epoxy |  | — | — | — | — | — | — | 100 |
| Phenol novolak |  | 51 | 52 | 46.9 | 46 | 53.6 | 45.7 | 55.5 |
| Triphenylphosphine |  | 1.5 | 1.5 | 1.5 | 1.5 | 1.5 | 1.5 | 1.5 |
| Fillers |  | 1359 | 1370 | 1322 | 1314 | 1382.3 | 1311.3 | 1400 |
| Carnauba wax |  | 3.28 | 3.31 | 3.19 | 3.17 | 3.34 | 3.17 | 3.38 |
| Silane coupling agent SH-6040 |  | 4.4 | 4.41 | 4.25 | 4.23 | 4.44 | 4.23 | 4.5 |
| Working properties |  | ◯ | ◯ | ◯ | ◯ | X | X | ◯ |
| Spiral flow | inch | 36 | 39 | 31 | 32 | 36 | Poor flow properties and incapable of preparing test pieces | 47 |
| Bardol hardness | — | 81 | 83 | 81 | 80 | 84 | | 83 |
| Glass transition temperature | 0° C. | 152 | 145 | 156 | 147 | 138 | | 135 |
| Bending strength | kg/cm$^2$ | 2.22 | 1.8 | 1.57 | 1.59 | 2.1 | | 1.66 |
| Bending modulus | kg/cm$^2$ | 166 | 141 | 138 | 131 | 179 | | 189 |
| Water absorption | % | 0.169 | 0.166 | 0.195 | 0.182 | 0.156 | | 0.183 |
| 72 hours | | | | | | | | |
| 168 hours | % | 0.207 | 0.202 | 0.213 | 0.21 | 0.194 | | 0.224 |
| 336 hours | % | 0.205 | 0.23 | 0.22 | 0.227 | 0.261 | | 0.25 |
| Solder cracking | % | 0 | 0 | 0 | 0 | 0 | | 0 |
| 72 hours | | | | | | | | |
| 168 hours | % | 0 | 0 | 0 | 0 | 20 | | 20 |
| 336 hours | % | 0 | 0 | 0 | 0 | 60 | | 80 |

Example 15 Synthesis of epoxy resin-14

An intermediate XMCE-20 and then a material phenol XMSB-20 were ((An intermediate XMCE-20 was)) obtained in the same manner as the processes (1) and (2) of Reference 3((Reference 3 (1))), except that 195.5 g (1.6 mol) of 26XY and 65.7 g (0.4 mol) of 3M6B were used in place of 244.4 g (2.0 mol) of 26XY. The process (3) of Reference 3 was repeated using 80.8 g of the material phenol XMSB-20 ((the intermediate XMCE-20 instead of XMSB-20)) and 62.36 g, instead of 61.71 g, of the 48.3% aqueous solution of sodium hydroxide, to give 96.4 g of final product (yield: 97%) (hereinafter referred to as XMCC-20E).

GPC (detected with a differential refractometer) showed that the purity of the product was 93.2% and the rate of the stilbene epoxy compound including the 26XY residue and the 3M6B residue ((26XY and 3M6B)) in its molecular structure was 39.5%. The product had the melting point of 110 through 130° C. and the epoxy equivalent weight of 208 g/eq. Infrared spectroscopy showed that the absorption due to the phenolic hydroxyl group disappeared and that the product had absorptions of 1240 cm−1 and 920 cm−1 due to the epoxy group. The hydrolytic chlorine was 280 ppm.

Compared with the conventional stilbene epoxy resin compositions, the stilbene epoxy resin composition of the present invention has better working and molding properties and advantages in the handling process. The stilbene epoxy resin composition of the present invention has low hygroscopicity and excellent heat resistance and is favorably used as material for encapsulating electronic parts. Resin-encapsulated semiconductor devices utilizing the resin composition of the present invention have high resistance against solder cracking and do not cause package cracks even after the long-time water absorption. The present invention accordingly provides a encapsulating material having high reliability without damaging the molding conditions and working properties of the conventional encapsulating materials.

What is claimed is:

1. A stilbene bisphenol represented by the general formula (1), in which two different aryl groups are bound to a carbon—carbon double bond,

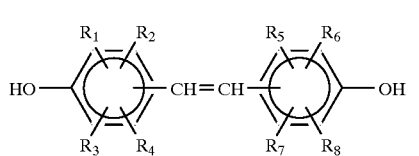

(1)

wherein $R_1$ through $R_8$ independently represent acyclic or cyclic alkyl groups having 1 through 6 carbon atoms, or hydrogen atom.

2. A bisphenol mixture comprising a stilbene bisphenol represented by the general formula (1) in claim 1, and a stilbene bisphenol represented by the general formula (3) given below in which two identical aryl groups are bound to a carbon—carbon double bond,

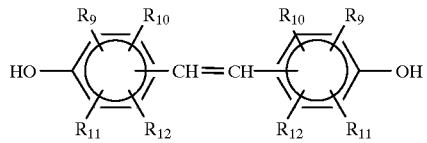

(3)

wherein $R_9$ through $R_{12}$ independently represent acyclic or cyclic alkyl groups having 1 through 6 carbon atoms, hydrogen atom or halogen atoms.

3. A stilbene bisphenol in accordance with claim 1, wherein $R_1$ represents a t-butyl group, and $R_5$ through $R_8$ represent independently acyclic alkyl groups other than t-butyl group, cyclic alkyl groups, or hydrogen atoms in the general formula (1) given above.

4. A method of preparing a bisphenol mixture of claim 2, said method comprising the steps of subjecting a 1,1-bis(hydroxyphenyl)-2-chloroethane derivative, which is obtained by a reaction of two or more phenols with chloroacetaldehyde in the presence of an acid substance, to a dehydrochlorination reaction and a rearrangement reaction in the presence of a basic substance.

5. A stilbene bisphenol according to claim 1, wherein $R_1$ represents a t-butyl group.

6. A stilbene bisphenol according to claim 1, wherein $R_5$ through $R_8$ represent, independently, acyclic alkyl groups other that a t-butyl group, cyclic alkyl groups, or hydrogen atoms.

7. A stilbene bisphenol according to claim 1, wherein said stilbene bisphenol is at least one of:

3-t-butyl-4,4'-dihydroxy-3'-methyl-stilbene,
3-t-butyl-4,4'-dihydroxy-5,3'-dimethyl-stilbene,
3-t-butyl-4,4'-dihydroxy-3',6-dimethylstilbene,
3-t-butyl-4,4'-dihydroxy-5-ethyl-3'-methylstilbene,
3-t-butyl-4,4'-dihydroxy-3'-methyl-5-propylstilbene,
3-t-butyl-4,4'-dihydroxy-5-butyl-3'-methyl-stilbene,
3-t-butyl-4,4'-dihydroxy-5-amyl-3'-methylstilbene,
3-t-butyl-4,4'-dihydroxy-5-hexyl-3'-methylstilbene,
3-t-butyl-4,4'-dihydroxy-5-cyclohexyl-3'-methylstilbene,
3-t-butyl-4,4'-dihydroxy-3',5,5'-trimethyl-stilbene,
3-t-butyl-2,4'-dihydroxy-3',5',6-trimethylstilbene,
3-t-butyl-4,4'-dihydroxy-3',5',6-trimethylstilbene,
3-t-butyl-4,4'-dihydroxy-3',5-dimethyl-5'-propylstilbene, or
3-t-butyl-4,4'-dihydroxy-3',6-dimethyl-5'-propylstilbene.

8. A stilbene bisphenol according to claim 1, wherein said stilbene bisphenol is at least one of:

3-t-butyl-4,4'-dihydroxy-3',5,5'-trimethylstilbene,
3-t-butyl-2,4'-dihydroxy-3',5',6-trimethylstilbene, or
3-t-butyl-4,4'-dihydroxy-3',5',6-trimethylstilbene.

* * * * *